United States Patent [19] [11] 4,264,425
Kimura et al. [45] Apr. 28, 1981

[54] DEVICE FOR DETECTION OF AIR/FUEL RATIO FROM OXYGEN PARTIAL PRESSURE IN EXHAUST GAS

[75] Inventors: Shinji Kimura, Yokohama; Hiroshi Takao, Kamakura; Shigeo Ishitani, Yokosuka; Kenji Ikezawa; Hiroyuki Aoki, both of Yokohama, all of Japan

[73] Assignee: Nissan Motor Company, Limited, Yokohama, Japan

[21] Appl. No.: 152,857

[22] Filed: May 23, 1980

[30] Foreign Application Priority Data

May 25, 1979 [JP] Japan ................................. 54-64062

[51] Int. Cl.³ ......................... G01N 27/58; F02M 7/00
[52] U.S. Cl. ................................. 204/195 S; 60/276; 123/489
[58] Field of Search .............. 204/195 S, 1 S; 422/98; 60/276; 123/489

[56] References Cited

U.S. PATENT DOCUMENTS 3,674,436 7/1972 Geul ................................. 422/98 X
4,207,159 6/1980 Kimura et al. ................... 204/195 S

*Primary Examiner*—G. L. Kaplan
*Attorney, Agent, or Firm*—Schwartz, Jeffery, Schwaab, Mack, Blumenthal & Koch

[57] ABSTRACT

A device having an oxygen sensing probe to be disposed in a combustion gas to detect actual air/fuel ratio values of an air-fuel mixture subjected to combustion. The probe is a combination of two oxygen concentration cells each having a porous solid electrolyte layer such as of zirconia, a porous measurement electrode layer on one side of the solid electrolyte layer and a reference electrode layer on the other side, with a shield layer thereon. Either the shield layers of the two cells or the solid electrolyte layers of the two cells are provided by a single layer which serves also as a substrate of the entire probe. The device includes DC power supply means for forcing a current to flow through the solid electrolyte of each cell thereby to cause oxygen ions to migrate through each solid electrolyte layer, from the reference electrode layer to the measurement electrode layer in one cell and reversely in the other cell. Both air/fuel ratios above a stoichiometric ratio inclusive and air/fuel ratios below the soichiometric ratio inclusive can be detected by this device.

17 Claims, 24 Drawing Figures

FIG. 16(A)     FIG. 16(B)     FIG. 16(C)
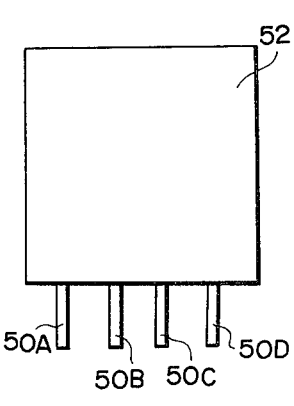 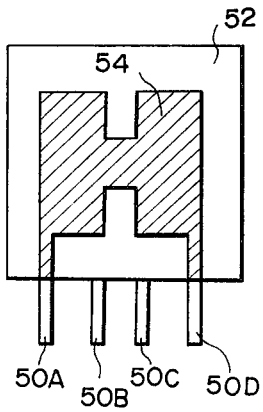 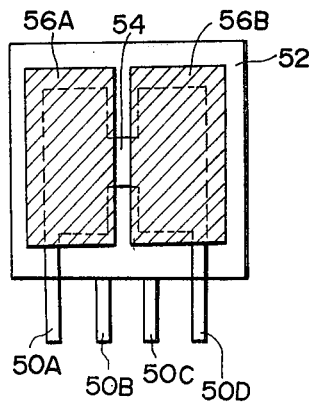
FIG. 16(D)     FIG. 16(E)
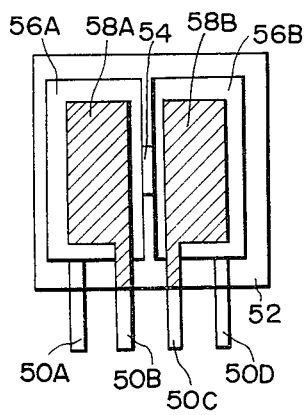 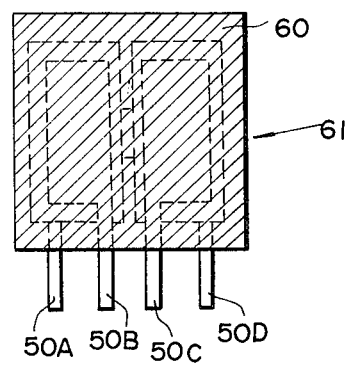

DEVICE FOR DETECTION OF AIR/FUEL RATIO FROM OXYGEN PARTIAL PRESSURE IN EXHAUST GAS

BACKGROUND OF THE INVENTION

This invention relates to a device for detecting an actual air/fuel ratio of an air-fuel mixture subjected to combustion in a combustor, such as the combustion chambers of an internal combustion engine, based on the magnitude of an oxygen partial pressure in the combustion gas exhausted from the combustor.

Recently a marked tendency to electronical control of internal combustion engines has been shown, particularly in the automobile industries, with a primary object of achieving an extremely minute control of the air/fuel ratio thereby improving the fuel economy and further reducing the emission of HC, CO and Nox by, for example, enhancing the efficiency of a three-way catalyst. In many cases an electronically controlled engine system includes an oxygen sensor to detect the concentration of oxygen in the exhaust gas as an indication of an actual air/fuel ratio of an air-fuel mixture supplied to the engine. For example, a feedback signal provided by the oxygen sensor is put into an electronic control circuit which provides a control signal to an electromagnetic flow control valve for minute control of the feed rate of either fuel or auxiliary air.

Oxygen sensors prevailing for this purpose are of the concentration cell type having a layer of an oxygen ion conductive solid electrolyte, such as $ZrO_2$ stabilized with CaO, a measurement electrode layer porously formed on one side of the solid electrolyte layer and a reference electrode layer formed on the other side. These oxygen sensors are designed and used such that a reference oxygen partial pressure is maintained on the reference electrode side by using a certain oxygen-containing substance, while the measurement electrode layer is exposed to the exhaust gas. When there occurs a change in the air/fuel ratio of an air-fuel mixture supplied to the engine across the stoichiometric air/fuel ratio, a great and sharp change is exhibited in the magnitude of an electromotive force the oxygen sensor in the exhaust gas generates. Accordingly this type of oxygen sensor is suitable to applications to engines operated with a stoichiometrical or nearly stoichiometrical air-fuel mixture. However, it is impossible to detect or estimate air/fuel ratio values of either a lean mixture or a rich mixture by the use of an oxygen sensor of this type in the exhaust gas because, when the air/fuel ratio varies but remains on one side of the stoichiometric ratio, the magnitude of the electromotive force exhibits only very small changes, if not changeless, compared with changes in the air/fuel ratio.

Meanwhile the development of so-called lean-burn engines has been in progress with the view of attaining a maximal thermal efficiency together with advancement of the exhaust emission control. Also, so-called richburn engines have attracted attention because of the possibility of achieving a very high mechanical efficiency. Accordingly there is a keen demand for an oxygen sensor which is to be used in exhaust gases (since it is more convenient to provide an oxygen sensor to the exhaust system of an engine than to the intake system) and enables to detect air/fuel values deviated from a stoichiometric ratio.

In our prior U.S. Patent Application Ser. No. 28,747 filed on Apr. 10, 1979 and now U.S. Pat. No. 4,224,113, we have proposed a method of detecting an actual air/fuel ratio of an air-fuel mixture, which may be either a lean mixture or a rich mixture, subjected to combustion in, for example, an internal combustion engine by disposing an oxygen sensitive probe, which is of the concentration cell type having a solid electrolyte layer sandwiched between a measurement electrode layer and a reference electrode layer which is covered with a shield layer, in the exhaust gas and forcing a constant DC current of an adequately predetermined intensity to flow through the solid electrolyte layer between the two electrode layers in a selected direction with the intention of constantly maintaining an appropriate magnitude of reference oxygen partial pressure at the interface between the reference electrode layer and the solid electrolyte layer by causing migration of oxygen ions through the solid electrolyte layer in a selected direction. (The particulars of this oxygen sensing probe will be described hereinafter.) Either air/fuel ratios above a stoichiometric ratio inclusive or air/fuel ratios below the stoichiometric ratio inclusive can be detected (depending on the direction of the flow of the DC current) by this method, but in the case of an engine or a combustor being operated sometimes with a rich mixture and at other times with a lean mixture it is impossible to detect every air/fuel ratio value realized in the engine by this method.

SUMMARY OF THE INVENTION

It is an object of the present invention to provide a device to detect actual air/fuel ratio values of an air-fuel mixture subjected to combustion in a combustor, such as an automotive internal combustion engine, based on the magnitude of an oxygen partial pressure in a combustion gas exhausted from the combustor, which device is simple in construction and has the capability of accurately detecting both air/fuel ratios above a stoichiometric air/fuel ratio inclusive and air/fuel ratios below the stoichiometric ratio inclusive.

An air/fuel ratio detecting device according to the invention comprises an oxygen sensing element having first and second oxygen concentration cells each constituted of a microscopically porous and gas permeable layer of an oxygen ion conductive solid electrolyte, a gas permeably porous measurement electrode layer formed on one side of the solid electrolyte layer, a reference electrode layer formed on the other side of the solid electrolyte layer and a shield layer which is made of an electrochemically inactive material and covers the reference electrode layer. In this oxygen sensing element, either the shield layers of the two cells or the solid electrolyte layers of the two cells are provided by a single layer which is shaped and dimensioned so as to serve also as a structurally basic member of the entire element. The device further comprises first potentiometer means for measuring an electromotive force generated by the first concentration cell, second potentiometer means for measuring an electromotive force generated by the second concentration cell and DC power supply means for forcing a DC current to flow through the solid electrolyte layer of each concentration cell from the measurement electrode layer to the reference electrode layer in the first concentration cell but from the reference electrode layer to the measurement electrode layer in the second concentration cell.

The flow of a DC current in each cell causes migration of oxygen ions through the solid electrolyte layer between the reference and measurement electrode layers in a direction reversely of the direction of the current flow. As a consequence, in the first cell a reference oxygen partial pressure of a relatively low magnitude can be maintained at the interface between the solid electrolyte layer and the reference electrode layer, whereas in the second cell a reference oxygen partial pressure of a relatively high magnitude can be maintained at the interface between the solid electrolyte layer and the reference electrode layer. Therefore, in a combustion gas produced from an air-fuel mixture containing excess air the first concentration cell generates an electromotive force of which magnitude greatly depends on the air/fuel ratio of the mixture, whereas in a combustion gas produced from a fuel-rich air-fuel mixture the second concentration cell generates an electromotive force of which magnitude greatly depends on the air/fuel ratio of the mixture.

Thus, a device according to the invention enables to accurately detect both air/fuel ratios above a stoichiometric ratio inclusive and air/fuel ratios below the stoichiometric ratio inclusive and accordingly is applicable to lean-burn engines, rich-burn engines and engines operated with a stoichiometrical or nearly stoichiometrical air-fuel mixture, and even to engines sometimes operated with a lean mixture and at other times with a rich mixture. Because of the capability of detecting air/fuel ratios in such a wide range and simpleness of the construction, this device is particularly suitable for applications to automotive engines and, besides, can be applied to various types of combustion apparatus as exemplified by industrial burners and household heating apparatus.

The oxygen sensing element in a device according to the invention can be designed in a variety of forms as will be illustrated in the following description of the preferred embodiments.

BRIEF DESCRIPTION OF THE DRAWINGS

FIGS. 16(A) to 16(E) illustrate an exemplary process of producing an air/fuel ratio detecting device according to the invention;

DESCRIPTION OF THE PREFERRED EMBODIMENTS

Prior to a detailed description of the present invention, a brief description will be given about a device used in the air/fuel ratio detecting method we have proposed in the above mentioned prior patent application with reference to FIG. 1.

Figure 1:
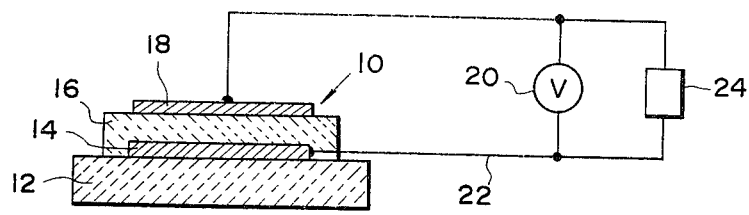
FIG. 1 shows schematically and sectionally a fundamental construction of a device used in an air/fuel ratio detection method we have previously proposed.

As a principal element of the device of FIG. 1, an oxygen sensing element 10 has a base plate or substrate 12 made of an electrochemically inactive material, a reference electrode layer 14 formed on one side of the substrate 12, a microscopically porous layer 16 of an oxygen ion conductive solid electrolyte formed on the same side of the substrate 12 so as to sandwich the reference electrode layer 14 therebetween and a microscopically porous measurement electrode layer 18 formed on the outer side of the solid electrolyte layer 16. Macroscopically, the reference electrode layer 14 is completely shielded from the environmental atmosphere, whereas the measurement electrode layer 18 can be exposed to a gas subject to measurement. Usually the substrate 12 is made to have a dense structure substantially impermeable to gases, so that the reference electrode layer 14 communicates with the environmental atmosphere through micropores in the measurement electrode layer 18 and solid electrolyte layer 16. As a modification, the solid electrolyte layer 16 can be designed as a sufficiently thick plate so as to serve as a structurally basic member of this element 10 while the substrate 12 is replaced by a far thinner layer which serves merely as a shield coating on the reference electrode layer 14. Therefore, the substrate 12 (and a corresponding layer in a device according to the present invention) will hereinafter be called a shield layer.

The reference and measurement electrode layers 14 and 18 are connected by leads 22 to a potentiometer 20 or an equivalent instrument to measure an electromotive force the element 10 generates when there is a difference in oxygen partial pressure between the reference electrode layer 14 and the measurement electrode layer 18. Furthermore, a DC power source 24 is connected to the two electrode layers 14, 18 in parallel with the potentiometer 20.

To detect actual values of the air/fuel ratio of an air-fuel mixture supplied to a combustion engine, the oxygen sensing element 10 is entirely disposed in the exhaust gas of the engine, and the DC power source 24 is used to force a constant DC current to flow through the solid electrolyte layer 16 between the reference electrode 14 and the measurement electrode 18 in order to cause controlled migration of oxygen ions through the solid electrolyte layer 16 and electrolytic reactions (including ionization of oxygen and formation of oxygen molecules from oxygen ions) on the respective sides of the solid electrolyte layer 16. The intensity of the DC current is made to be below a certain critical value, and the direction of the flow of the current is chosen depending on the type of the air-fuel mixture. In the case of an engine operated with a lean mixture, the current is made to flow from the measurement electrode layer 18 to the reference electrode layer 14, whereas in the case of a rich mixture the current is made to flow from reference electrode layer 14 to the measurement electrode layer 18. In either case, an ultimate effect of the flow of the current is the establishment of a stable reference oxygen partial pressure of a desirable magnitude at the interface between the solid electrolyte layer 16 and the reference electrode layer 14.

When the device of FIG. 1 is applied to an engine exhaust gas produced from a lean mixture with the supply of a DC current in the aforementioned direction, the magnitude of electromotive force (EMF) generated by the oxygen sensing element 10 becomes maximal when the air/fuel ratio is close to (but above) the stoichiometric ratio and gradually lowers as the air/fuel ratio becomes higher, so that it is possible to precisely detect air/fuel ratio values of the lean mixture. If, however, the air/fuel ratio becomes below the stoichiometric ratio, the element 10 does not generate an appreciable magnitude of EMF. Therefore, it is impossible to detect air/fuel ratio values of rich mixture by a device of FIG. 1 designed for a lean mixture. When the direction of the flow of the current is made appropriate to the application of this device to an engine exhaust gas produced from a rich mixture, the magnitude of EMF generated by the element 10 becomes maximal when the air/fuel ratio is close to (but below) the stoichiometric ratio and gradually lowers as the air/fuel ratio lowers, so that air/fuel ratio values of the rich mixture can precisely be detected. However, in this case the magnitude of the EMF becomes very small and useless for detection of actual air/fuel ratio values if the air/fuel ratio becomes above the stoichiometric ratio.

The present invention has been made on the basis of our knowledge of advantages and limitations of the device of FIG. 1.

Figure 2:
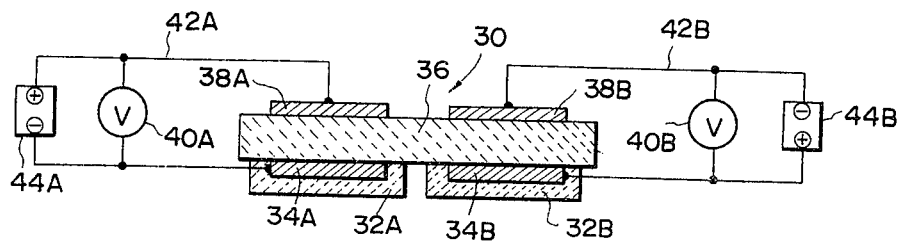
FIG. 2 is a schematic and sectional illustration of an air/fuel ratio detecting device as an embodiment of the present invention.

FIG. 2 shows an air/fuel ratio detecting device embodying the present invention. In this device, an oxygen sensing element 30 has a layer 36 of an oxygen ion conductive solid electrolyte in the form of a rigid plate thick enough to serve as a structurally basic member of this element 30. A thin first reference electrode layer 34A is formed on one side of the solid electrolyte layer 36 so as to occupy a limited portion of the entire surface area of the layer 36, and a first shield layer 32A is formed on the same side of the solid electrolyte layer 36 so as to entirely cover the electrode layer 34A. On the opposite side of the solid electrolyte layer 36, a thin, microscopically porous and gas permeable first measurement electrode layer 38A is formed so as to occupy a limited area and lie generally opposite to the reference electrode layer 34A.

Spaced from the first reference electrode layer 34A, but on the same side, a thin second reference electrode layer 34B is formed on the solid electrolyte layer 36, and a second shield layer 32B covers this electrode layer 34B entirely. On the opposite side of the solid electrolyte layer 36, a thin, microscopically porous and gas permeable second measurement electrode layer 38B is formed so as to be spaced from the first measurement electrode layer 38A and lie generally opposite to the second reference electrode layer 34B.

Thus, this oxygen sensing element 30 can be regarded as a combination of two sets of oxygen concentration cells: that is, one constituted of a part of the solid electrolyte layer 36, the first measurement electrode layer 38A, the first reference electrode layer 34A and the first shield layer 32A; and the other constituted of a part of the solid electrolyte layer 36, the second measurement electrode layer 38B, the second reference electrode layer 34B and the second shield layer 32B.

The first reference electrode layer 34A and the first measurement electrode layer 38A are connected by leads 42A to a first potentiometer 40A or an equivalent instrument to measure an electromotive force generated across the solid electrolyte layer 36 between these two electrode layers 34A and 38A, and also a first DC power source 44A is connected to these two electrode layers 34A and 38A in parallel with the potentiometer 40A so as to force a DC current to flow through the solid electrolyte layer 36 from the measurement electrode layer 38A towards the reference electrode layer 34A. The second reference electrode layer 34B and the second measurement electrode layer 38A are connected by leads 42B to a second potentiometer 40B (or an equivalent instrument) to measure an EMF generated across the solid electrolyte layer 36 between these two electrode layers 34B and 38B. In parallel with the potentiometer 40B, a second DC power source 44B is connected to the two electrode layers 34B and 38B so as to force a current to flow through the solid electrolyte layer 36 from the reference electrode layer 34B towards the measurement electrode layer 38B. The solid electrolyte layer 36 is made to have a microscopically porous and gas permeable structure so that the macroscopically shielded reference electrode layers 34A and 34B can communicate with the environmental atmosphere. Preferably the DC power sources 44A and 44B are of the constant current type. Actually a device according to the invention has switches, but they are omitted from illustration. Practical materials for the respective layers of the oxygen sensitive element 10 will be described later.

To detect actual air/fuel ratio values of an air-fuel mixture supplied to, for example, an automotive engine by using the device of FIG. 2, the oxygen sensing element 30 is disposed in the exhaust passage at a location where the exhaust gas temperature is sufficiently high.

The exhaust gas contacts not only the measurement electrode layers 38A, 38B but also the reference electrode layers 34A, 34B. Since the first measurement electrode layer 38A and first reference electrode layer 34A are respectively connected to the positive and negative terminals of the first DC power source 44A, at the interface between the reference electrode layer 34A and the solid electrolyte layer 36 there occurs an electrolytic reaction expressed by:

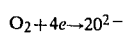

The $O^{2-}$ ions formed by this reaction migrate through the solid electrolyte layer 36 towards the first measurement electrode layer 38A, and at the interface between this electrode layer 38A and the solid electrolyte layer 36 there occurs a reaction expressed by:

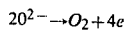

Figure 3:
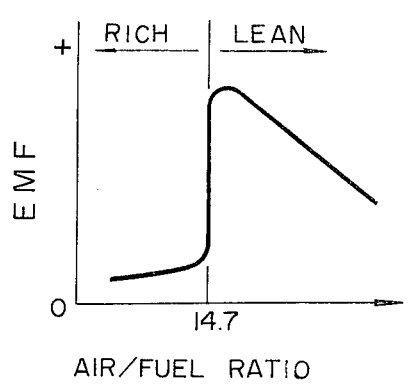
FIGS. 3-6 are graphs for the explanation of the output characteristic of the device of FIG. 2 in an engine exhaust gas.

These phenomena result in outflow of oxygen from the first reference electrode layer 34A into the exterior exhaust gas and accordingly lowering of oxygen partial pressure at the interface between the reference electrode layer 34A and the solid electrolyte layer 36. Therefore, the magnitude of EMF generated by an oxygen concentration cell constituted of the solid electrolyte layer 36, first reference electrode 34A and first measurement electrode 38A remains very small if the air-fuel mixture is a rich mixture, that is, the air/fuel ratio is below a stoichiometric ratio (about 14.7 for an air-gasoline mixture). When the air-fuel mixture is a lean mixture, the magnitude of EMF generated by the same concentration cell becomes considerably great and exhibits a practically linear relation with the air/fuel ratio, as shown in FIG. 3, conditioning that the intensity of the DC current flowing through the solid electrolyte layer 36 from the measurement electrode 38A towards the reference electrode 34A is adequate. If the current intensity is too low, it is natural that the magnitude of EMF remains too small and scarcely depends on the air/fuel ratio. However, the current intensity should not be excessively high because there is a critical current intensity above which the magnitude of EMF becomes substantially constant (and maximal) irrespective of air/fuel rato values of a lean mixture. Generally, such a critical current intensity is in the range from about 3 $\mu A$ to about 20 $\mu A$. The DC power source 44A is designed so as to supply a constant current of which intensity is sufficiently high but below such a critical current intensity.

Figure 4:
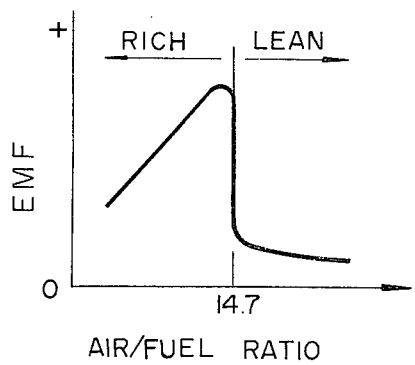

The second reference electrode layer 34B and the second measurement electrode layer 38B are respectively connected to the positive and negative terminals of the second DC power source 44B. That is, the connection of these electrodes 34B and 38B to the DC power source 44B is reversely of the connection of the electrodes 34A and 38A to the DC power source 44A. Accordingly, at the interface between the second measurement electrode layer 38B and the solid electrolyte layer 36 there occurs ionization of oxygen molecules: $O_2 + 4e \rightarrow 2O^{2-}$ These $O_2^{2-}$ ions migrate through the solid electrolyte layer 36 towards the second reference electrode layer 34B, and at the interface between the solid electrolyte layer 36 and the reference electrode layer 34B there occurs a reaction expressed by $2O^{2-} \rightarrow O_2 + 4e$ These phenomena result in inflow of oxygen from the exterior exhaust gas to the second reference electrode layer 34B and accordingly a rise in oxygen partial pressure at the interface between this electrode layer 34B and the solid electrolyte layer 36. Therefore, the magnitude of EMF generated by an oxygen concentration cell constituted of the solid electrolyte layer 36, second reference electrode 34B and second measurement electrode 38B remains very small if the air/fuel mixture supplied to the engine is a lean mixture. When the air-fuel mixture is a rich mixture, the magnitude of EMF generated by the same concentration cell becomes considerably large and exhibits a practically linear relation with the air/fuel ratio, as shown in FIG. 4, conditioning that the intensity of the current flowing through the solid electrolyte layer 36 from the reference electrode 34B to the measurement electrode 38B is sufficiently high but below a critical current intensity (usually in the range from about 3 $\mu A$ to about 20 $\mu A$) above which the magnitude of EMF becomes substantially constant (and maximal) irrespective of air/fuel ratio values of a rich mixture. Accordingly the second DC power source 44B is designed so as to supply a constant current of an adequately predetermined intensity.

Figure 5:
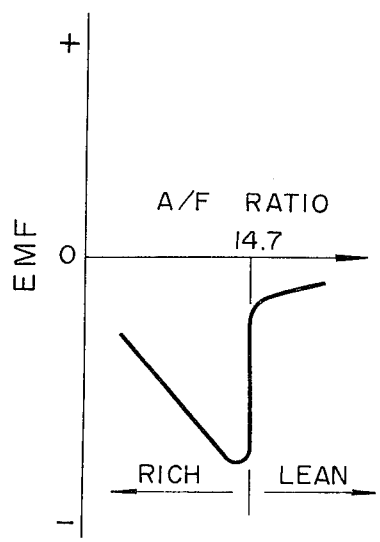
Figure 6:
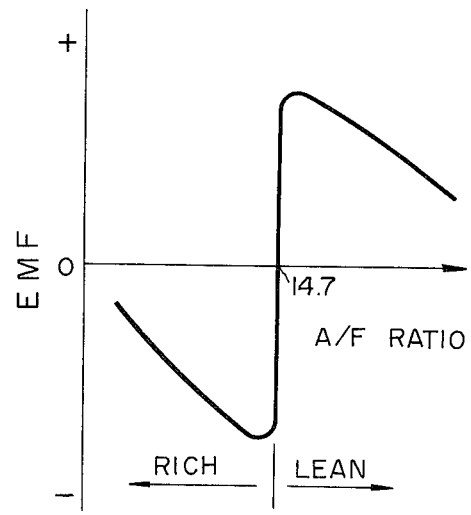

The polarity of the EMF which is related to the air/fuel ratio in the manner as shown in FIG. 4 and measured by the second potentiometer 40B can be inverted to give a characteristic curve as shown in FIG. 5 by inverting the polarity in connecting this potentiometer 40B with the electrodes 34B and 38B. Then, the device of FIG. 2 as a whole exhibits an output characteristic as shown in FIG. 6, given by combining the characteristic curve of FIG. 3 with the characteristic curve of FIG. 5. Therefore, this device has the capability of precisely detecting air/fuel values in a very wide range extending from a stoichiometric air/fuel ratio both towards the lean side and towards the rich side, meaning that this device is applicable to various types of engines or other kinds of combustion apparatus practically regardless of the air/fuel ratio value of an air-fuel mixture supplied to the apparatus, even to an apparatus which is operated sometimes with a rich mixture and at other times with a lean mixture.

Figure 7:
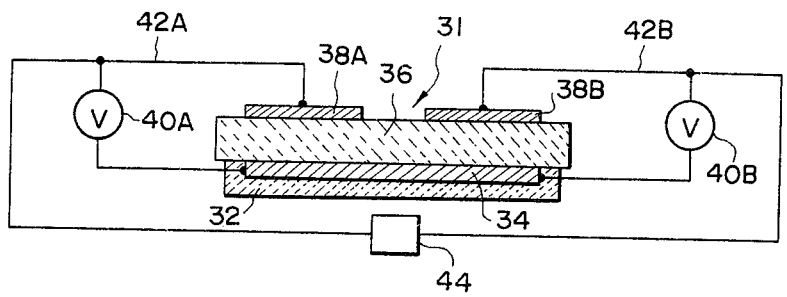
FIGS. 7-15 show, all in a schematic and sectional view similar to FIG. 2, nine differently designed air/fuel ratio detecting devices embodying the present invention, respectively.

FIG. 7 shows a second embodiment of the present invention. An oxygen sensing element 31 in this device differs from the element 30 of the device of FIG. 3 only in that the first and second reference electrode layers 34A and 34B in FIG. 2 are united into a single reference electrode layer 34 and that, in place of the two shield layers 32A and 32B in FIG. 2, a single shield layer 32 covers the reference electrode layer 34 completely. The first potentiometer 40A is connected to the reference electrode layer 34 and the first measurement electrode layer 38A, and the second potentiometer 40B to the reference electrode layer 34 and the second measurement electrode layer 38B. In this device it suffices to use a single DC power source 44 which is connected to the first and second measurement electrode layers 38A and 38B. For example, assume that the first measurement electrode layer 38A is connected to the positive terminal of the DC power source 44 and the second measurement electrode layer 38B to the negative terminal. Then, in a region covered with the first measurement electrode layer 38A oxygen ions migrate through the solid electrolyte layer 36 from the reference electrode layer 34 towards the first measurement electrode layer 38A, but in a region covered with the second measurement electrode layer 38B, oxygen ion migrates from this electrode layer 38B toward the reference electrode layer 34. Therefore, the output characteristic of this device in an exhaust gas is identical with that of the device of FIG. 2, as shown in FIG. 6.

Figure 8:
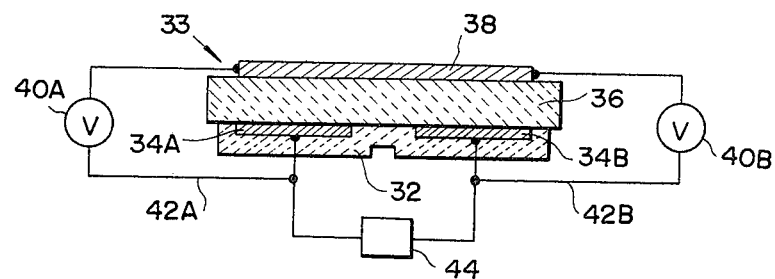

FIG. 8 shows a third embodiment of the invention. An oxygen sensing element 33 of this device differs from the element 30 of FIG. 2 only in that the first and second measurement electrode layers 38A and 38B in FIG. 2 are united into a single measurement electrode layer 38. Also in this case it suffices to use a single DC power source 44 which is connected to the first and second reference electrode layers 34A and 34B. In a region covered with the first reference electrode layer 34A there occurs migration of oxygen ions through the solid electrolyte layer 36 for example, from this electrode layer 34A towards the measurement electrode layer 38, while in a region covered with the second reference electrode layer 34B oxygen ions migrate in the opposite direction. Therefore, in an exhaust gas this device too exhibits an output characteristic as shown in FIG. 6.

Figure 9:
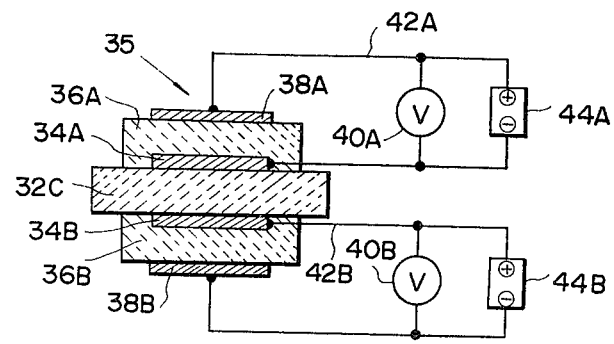

FIG. 9 shows a fourth embodiment of the invention. An oxygen sensing element 35 in this device has a single shield layer 32C which takes the form of a plate thick enough to serve as a structurally basic member of this element 35. On one side of the shield layer 32C, a first reference electrode layer 34A, first solid electrolyte layer 36A and first measurement electrode layer 38A are formed in the same arrangement as the corresponding layers 14, 16 and 18 in the device of FIG. 1. On the opposite side of the shield layer 32C, a second reference electrode layer 34B, second solid electrolyte layer 36B and second measurement electrode layer 38B are formed generally symmetrically with the first three layers 34A, 36A and 38A. A first potentiometer 40A is connected to the first reference electrode layer 34A and first measurement electrode layer 38A, and a first DC power source 44A is connected to these electrode layers 34A and 38A so as to force a constant DC current to flow through the solid electrolyte layer 36A, from the measurement electrode layer 38A towards the reference electrode layer 34A. A second potentiometer 40B is connected to the second reference electrode layer 34B and the second measurement electrode layer 38B, and a second DC power source 44B is connected to these electrode layers 34B and 38B so as to force a constant DC current to flow from the reference electrode layer 34B towards the measurement electrode layer 38B. As will be understood from the description of the construction, in an exhaust gas the device of FIG. 9 also exhibits an output characteristic as shown in FIG. 6.

Figure 10:
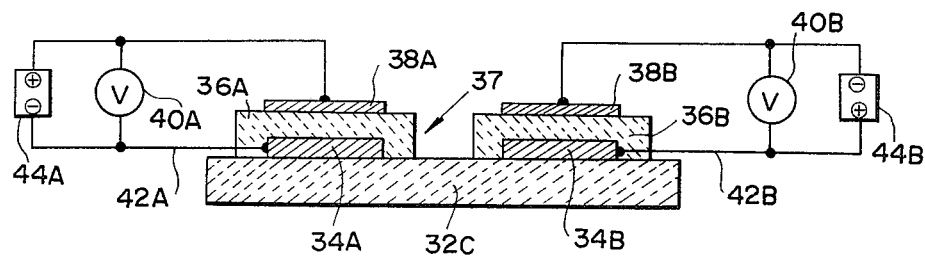

In a fifth embodiment of the invention shown in FIG. 10, an oxygen sensing element 37 differs from the element 35 of FIG. 9 only in that the first oxygen concentration cell, i.e. the combination of the three layers 34A, 36A, 38A, and the second cell, i.e. the combination of the three layers 34B, 36B, 38B, are formed on the same side of the shield layer 32C with a distance therebetween. Naturally the output characteristic of the device of FIG. 10 is identical with that of the device of FIG. 9.

Figure 11:
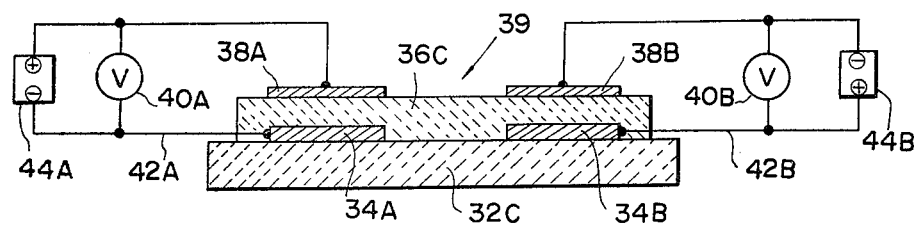

A sixth embodiment of the invention shown in FIG. 11 has an oxygen sensing element 39 which is almost identical with the element 37 of FIG. 10. As a sole difference, the first and second solid electrolyte layers 36A and 36B in FIG. 10 are united into a single solid electrolyte layer 36C in FIG. 11. It will be apparent that this modification has no influence on the output characteristic of the device.

Figure 12:
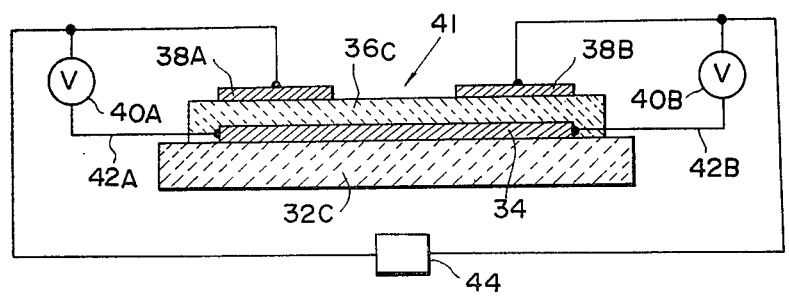

A seventh embodiment of the invention shown in FIG. 12 has an oxygen sensing element 41 which differs from the element 39 of FIG. 11 only in that the first and second reference electrode layers 34A and 34B in FIG. 11 are united into a single reference electrode layer 34. Because of this modification, the two DC power sources 44A, 44B in the device of FIG. 11 are replaced by a single DC power source 44 which is connected to the first and second measurement electrode layers 38A and 38B. In principle, the device of FIG. 12 is identical with the device of FIG. 7 and of cource exhibits an output characteristic as shown in FIG. 6.

Figure 13:
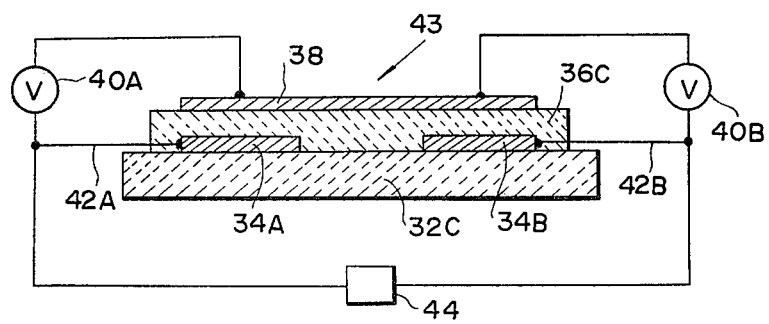

In an eighth embodiment of the invention shown in FIG. 13, an oxygen sensing element 43 differs from the element 39 of FIG. 11 only in that the two measurement electrode layers 38A and 38B in FIG. 11 are united into a single measurement electrode layer 38. Because of this modification, the device of FIG. 13 has only one DC power source 44 which is connected to the first and second reference electrode layers 34A and 34B. In principle, and hence in the function, this device is identical with the device of FIG. 8.

Figure 14:
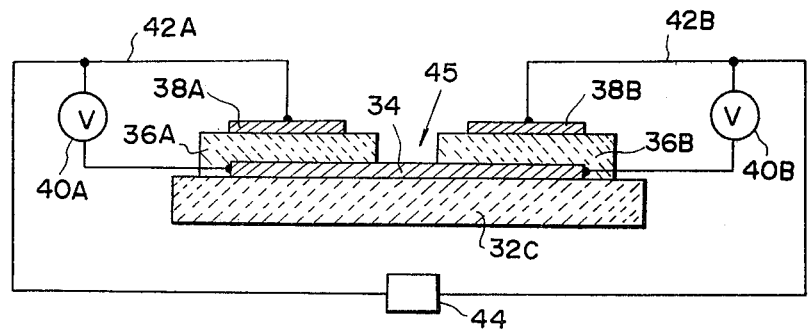

FIG. 14 shows a ninth embodiment of the invention, which can be regarded as a minor modification of the device of FIG. 12. That is, an oxygen sensing element 45 of this device is the result of cutting the single solid electrolyte layer 36C in the element 41 of FIG. 12 into a first solid electrolyte layer 36A provided with the first measurement electrode layer 38A and a second solid electrolyte layer 36B provided with the second measurement electrode layer 38B. It will be understood that this modification does not cause any change in the output characteristic of the device.

Figure 15:
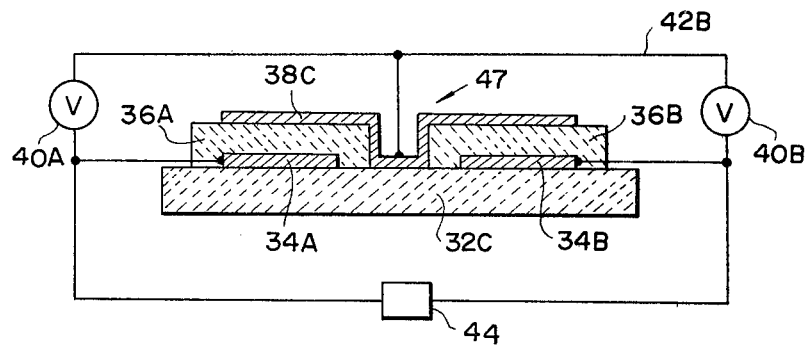

FIG. 15 shows a tenth embodiment of the invention, having an oxygen sensing element 47 which differs from the element 37 of FIG. 10 only in that the two measurement electrode layers 38A and 38B in FIG. 10 are united into a single measurement electrode layer 38C. Because of this modification, the device of FIG. 15 has only one DC power source 44 which is connected to the first and second reference electrode layers 34A and 34B. In principle and hence in the function, the device of FIG. 15 is identical with the device of FIG. 8 or the device of FIG. 13.

For every one of the oxygen sensing elements shown in FIGS. 2 and 7-15, it is optional to provide a porous protective coating which covers the outer surfaces of the measurement electrode layers, optionally together with the outer surfaces of the solid electrode layers, or the entire outer surfaces of the oxygen sensing element.

The material of each solid electrolyte layer (36) is selected from oxygen ion conductive solid electrolyte materials known as useful for conventional oxygen sensors of the concentration cell type. Some examples are $ZrO_2$ stabilized with CaO, $Y_2O_3$, SrO, MgO, $ThO_2$, $WO_3$ or $Ta_2O_5$; $Bi_2O_3$ stabilized with $Nb_2O_5$, SrO, $WO_3$, $Ta_2O_5$ or $Y_2O_3$; $ThO_2$-$Y_2O_3$ system; and CaO-$Y_2O_3$ system. In the case of using the solid electrolyte layer (36) as a structurally basic member of the oxygen sensing element, this layer (36) can be made, for example, by sintering of a press-moulded powder material or sintering of a so-called green sheet obtained by moulding or extrusion of a wet composition of which principal component is a powdered solid electrolyte material. In the case of using a shield layer (32) as the substrate of the oxygen sensing element, each solid electrolyte layer (36) can be formed as a relatively thin film-like layer by a physical deposition technique such as sputtering or ion plating, or by an electromechanical technique typified by plating, or by printing of a paste containing a powdered solid electrolyte material onto the substrate, followed by firing of the paste-printed substrate.

Each shield layer (32) is usually made of an electrically insulating ceramic material such as alumina, mullite, spinel or forsterite, but, in the case of an oxygen sensing element having only one reference electrode layer (34), use may be made of an electrically conducting material such as a corrosion-resistant metal element or alloy. This means that a cermet or a metal-ceramics mixture, too, is of use for the shield layer. When made to serve as the substrate of the oxygen sensing element, the shield layer is made, for example, by sintering of either a green sheet or a press-formed powder material, or by machining a body of a selected material. When a solid electrolyte layer (36) is used as a structurally basic member of the element, each shield layer may be formed as a relatively thin layer, for example, by plasma spraying or by printing a paste containing a powdered ceramic or metal onto the solid electrolyte layer and then sintering the printed paste layer.

It is preferable to embed an electrical resistance heating element in a shield layer (32) of the oxygen sensitive element according to the invention since oxygen ion conductivity of a solid electrolyte becomes very low when the solid electrolyte is not sufficiently heated. By the provision of a heater in the shield layer it becomes possible to achieve accurate detection of air/fuel ratio values of an air-fuel mixture supplied to an internal combustion engine even under low exhaust temperature conditions during a starting phase of the operation.

Each of the reference and measurement electrode layers (34,38) is made of an electronically conductive material selected from electrode materials for conventional solid electrolyte oxygen sensors. Examples are metals of the platinum group, which exhibit a catalytic activity on oxidation reactions of hydrocarbons, carbon monoxide etc., such as Pd, Ru, Rh, Os, Ir and Pt, including alloys of these platinum grup metals and alloys of a platinum group metal with a base metal, and some other metals and oxide semiconductors such as Au, Ag, SiC, $TiO_2$, CoO and $LaCrO_3$ which do not exhibit a catalytic activity on the aforementioned oxidation reactions. Each electrode layer is formed on a shield layer or a solid electrolyte layer as a relatively thin film-like layer, for example, by a physical deposition technique such as sputtering, vacuum evaporation, or ion plating, or by an electromechanical technique such as a plating, or by printing of a conductive paste, followed by firing of the printed paste layer.

For the aforementioned porous protective coating, use is made of a heat-resistant and electrically insulating material such as alumina, spinel or calcium zirconate ($CaO-ZrO_2$). The porous protective coating may be made, for example, by plasma spraying or by immersing the oxygen sensing element in a slurry of a selected powder material and then firing the slurry-impregnated element.

EXAMPLE

FIGS. 16(A) to 16(E) show a process of fabricating an oxygen sensing element 61 which is fundamentally similar to the element 45 of FIG. 14.

Referring to FIG. 6(A), a single shield layer 52 of this element 61 was an about 12×12 mm wide and 1.0 mm thick plate of alumina, and four platinum wires 50A, 50B, 50C, 50D were attached to this plate 52 so as to serve as leads 42A and 42B in FIG. 14. A paste containing a platinum powder dispersed in an organic medium was printed onto one side of the alumina plate 52 in a pattern as illustrated in FIG. 6(B) such that the printed paste layer extended to the platinum wires 50A and 50D, and, after drying of the printed paste layer at 100° C. for about 1 hr, the paste-printed plate 52 was fired in air at 1400° C. for 1 hr thereby to form a reference electrode layer 54 having a thickness of 2-3 μm. Then, a solid electrolyte paste prepared by dispersing 1 part by weight of a finely powdered $ZrO_2-Y_2O_3$ system (92:8 by weight) in 1 part by weight of an organic medium (lacquer) was printed onto the alumina plate or shield layer 52 so as to form two paste layers, with a gap therebetween as illustrated in FIG. 16(C), each covering about a half area of the reference electrode layer 54. After drying in air at 100° C. for about 1 hr, the paste-printed shield layer 52 was again fired in air at 1300° C. for 1 hr to sinter the solid electrolyte powder in the paste into two solid electrolyte layers 56A and 56B which were microscopically porous and 30-35 μm in thickness. Next, porous first and second measurement electrode layers 58A and 58B of platinum (shown in FIG. 16(D)) were formed respectively on the first and second solid electrolyte layers 56A and 56B by the method used to form the reference electrode layer 54 except that the firing temperature was lowered to 1300° C. These measurement electrode layers 58A, 58B were 2-3 μm in thickness. As can be seen in FIG. 16(D), the first and second measurement electrode layers 58A and 58B were respectively made to extend to the platinum wires 50B and 50C. Finally the element in the state of FIG. 16(D) was entirely coated with a porous protective layer 60 of calcium zirconate, as shown in FIG. 16(E), which was formed by plasma spraying.

Figure 17:
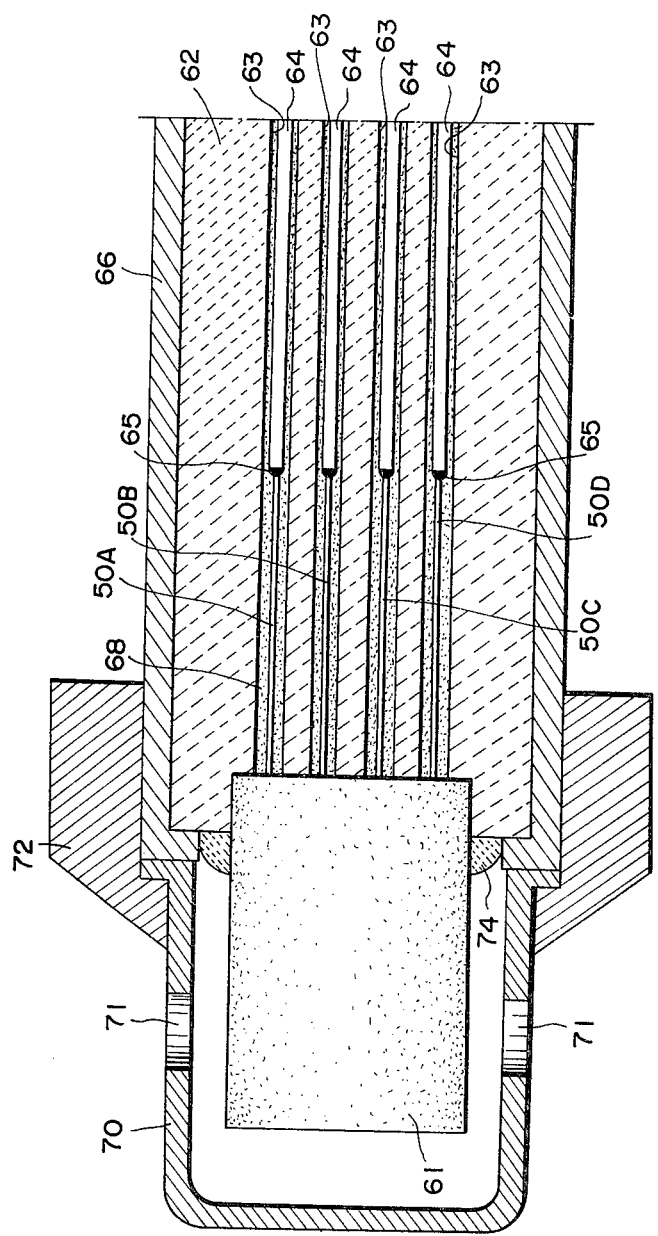
FIGS. 17 and 18 show, in a longitudinal sectional view, a practical and exemplary air/fuel ratio detecting device according to the invention.
Figure 18:
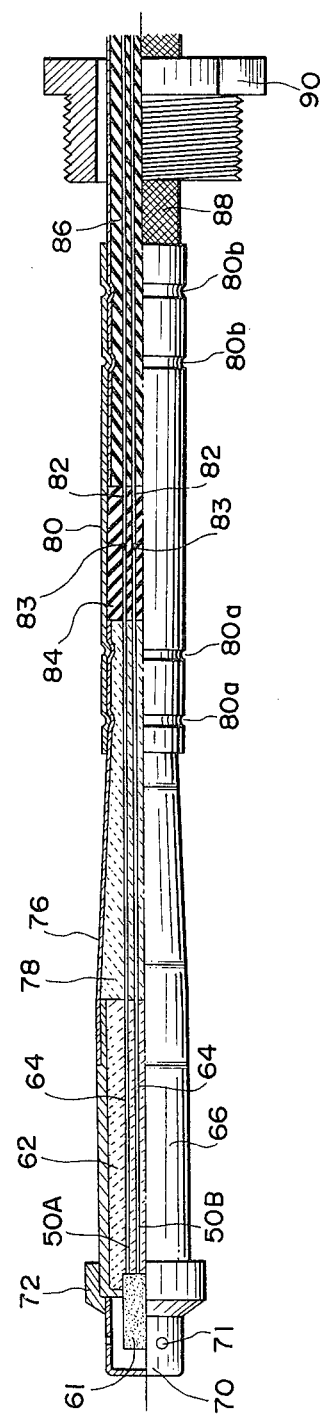

A practicable oxygen sensing probe as shown in FIGS. 17 and 18 was assembled by using the oxygen sensing element 61 of FIG. 16(E). The element 61 was mounted on an alumina rod 62 having four axial bores 63 by using a ceramic adhesive 74 of which principal component was $SiO_2$, and the platinum wires 50A, 50B, 50C and 50D were respectively welded (indicated at 65) to nickel wires 64 which were passed through bores 63 in the alumina rod 62. Thereafter the bores 63 were filled with a ceramic adhesive 68 to provide a gas-tight structure. The alumina rod 62 was tightly inserted into a tubular holder 66 of stainless steel, and a stainless hood 70 formed with apertures 71 was attached to the forward end of the holder 66 so as to enclose the oxygen sensing element 61 therein. Using a stainless ring 72, the hood 70 was welded to the holder 66. In a rear end portion, the holdr 66 was welded to another tubular holder 76 the interior of which was filled with alumina powder 78 to prevent shorting of the nickel wires 64 extending therethrough. In a rear end portion this holder 76 was fixed to a stainless steel pipe 80 by circumferential crimping as indicated at 80a. By using a silver solder, the nickel wires 64 were soldered to copper wires 82, as indicated at 83, which were extended through the interior of the pipe 80. To prevent outflow of the alumina powder 78 and shorting of the nickel wires 64 or the cupper wires 82, a forward portion of the interior of the pipe 80 was occupied by a separator 84 of silicone rubber, and an elongate plug of silicone rubber 86 was partially inserted into the pipe 80 from its rear end. This plug 86 was jacketed with a tubular wire braid 88 and then fixed to the pipe 80 by circumferential crimping as indicated at 80b. The jacketed plug 86 was made to loosely pass through a threaded nut 90 which could be moved to the rear end of the stainless ring 72 at the time of attaching this probe to, for example, an exhaust pipe of an automotive engine.

Figure 19:
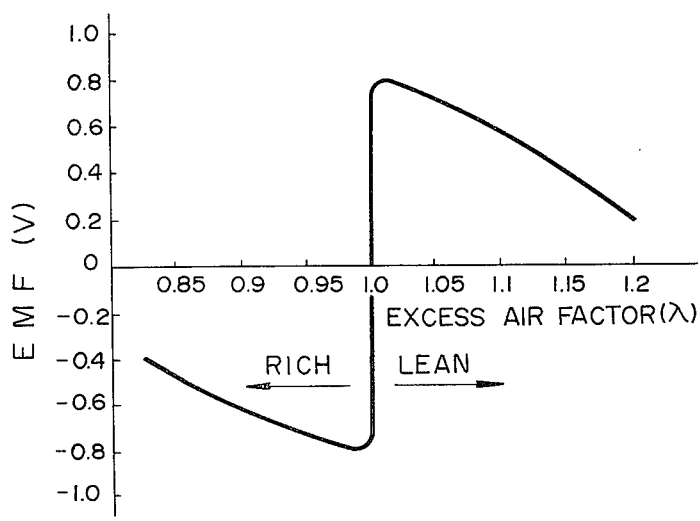
FIG. 19 is a graph showing the result of an experiment to examine the dependence of an electromotive force a device according to the invention generates in an engine exhaust gas on the excess air factor of an air-fuel mixture supplied to the engine.

The probe of FIG. 18 containing the oxygen sensing element 61 produced in the Example was attached to an exhaust pipe of an automotive gasoline engine so that the element 61 was exposed to the exhaust gas through the apertures 71 of the hood 70, and a DC power supply was connected to the two lead wires 50B and 50C in FIG. 16(E) so as to force a constant current of 3 μA to flow through each of the two solid electrolyte layers 56A and 56B. To examine the performance of the air/fuel ratio detecting device, the air/fuel ratio of an air-gasoline mixture for operation of the engine was varied within the range from about 0.8 to about 1.2 in terms of excess air factor. The exhaust gas temperature at the location of the probe was maintained constantly at 600° C. The result of this experiment is shown in FIG. 19. As can be seen in this graph, the output of the oxygen sensing element 61 was an exact indication of an actual air/fuel ratio whether the air/fuel ratio was equal to, higher than or lower than the stoichiometric ratio (excess air factor $\lambda = 1.0$).

Figure 20:
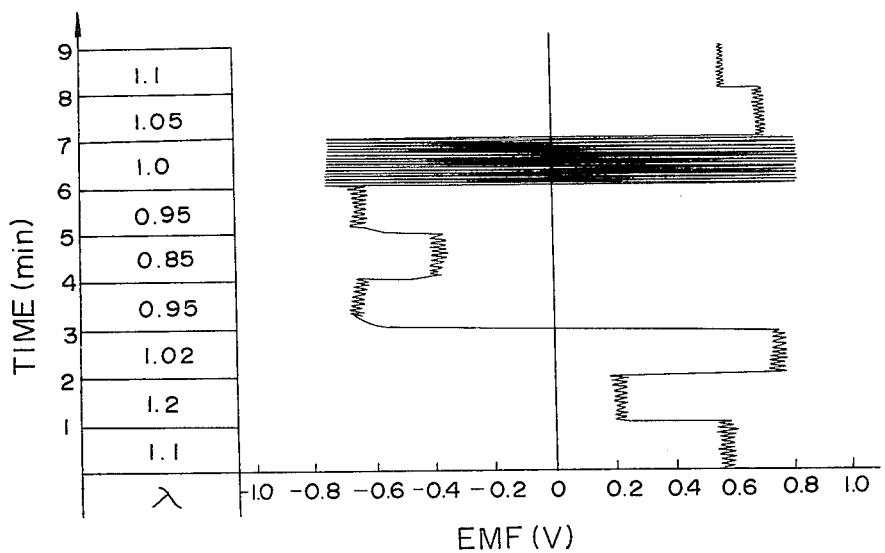
FIG. 20 is a chart showing the result of an additional experiment to examine the responsiveness of the device mentioned regarding FIG. 19 to periodic changes in the excess air factor of the above mentioned air-fuel mixture.

In a next experiment which was carried out by using the same engine and the air/fuel ratio detecting device as in the above described experiment, the air/fuel ratio of the air-gasoline mixture was varied in an irregular sequence as shown in FIG. 20 at intervals of one minute, but the exhaust gas temperature at the location of the probe 61 was constantly maintained at 600° C. The result recorded by an oscillograph is shown in FIG. 20. This chart demonstrates the existence of a very close relationship between the air/fuel ratio and the magnitude of EMF generated by the tested device over a very wide range of the air/fuel ratio and a very good responsiveness of the same device to changes in the air/fuel ratio.

What is claimed is:

1. A device to detect an actual air/fuel ratio of an air-fuel mixture subjected to combustion in a combustor based on the magnitude of an oxygen partial pressure in a combustion gas exhausted from the combustor, the device comprising:

an oxygen sensing element comprising first and second oxygen concentration cells each constituted of a microscopically porous and gas permeable solid electrolyte layer of an oxygen ion conductive solid electrolyte, a gas permeable porous measurement electrode layer formed on one side of the solid electrolyte layer, a reference electrode layer formed on the other side of the solid electrolyte layer and a shield layer of an electrochemically inactive material formed on said other side of the solid electrolyte layer such that macroscopically the reference electrode layer is entirely shielded from an environmental atmosphere by the shield layer and the solid electrolyte layer, one of (a) the shield layers of the first and second concentration cells and (b) the solid electrolyte layers of the first and second concentration cells being provided by a single layer which is so shaped and dimensioned as to serve as a structurally basic member of the entire element;

first potentiometer means for measuring an electromotive force generated by the first concentration cell;

second potentiometer means for measuring an electromotive force generated by the second concentration cell; and DC power supply means for forcing a DC current of a first predetermined intensity to flow through the solid electrolyte layer of the first concentration cell from the measurement electrode layer to the reference electrode layer and a DC current of a second predetermined intensity to flow through the solid electrolyte layer of the second concentration cell from the reference electrode layer to the measurement electrode layer.

2. A device according to claim 1, wherein said first predetermined intensity of the current is smaller than a first critical current intensity above which the magnitude of the electromotive force generated by the first concentration cell becomes substantially constant so long as said air/fuel ratio remains above the stoichiometric air/fuel ratio of said air/fuel mixture, said second predetermined intensity of the current being smaller than a second critical current intensity above which the magnitude of the electromotive force generated by the second concentration cell becomes substantially constant so long as said air/fuel ratio remains below said stoichiometric air/fuel ratio.

3. A device according to claim 1, wherein the measurement electrode layers of the first and second concentration cells are provided by a single electrode layer.

4. A device according to claim 1, wherein the reference electrode layers of the first and second concentration cells are provided by a single electrode layer.

5. A device according to claim 1, wherein the first and second concentration cells are arranged generally symmetrically with respect to a plane perpendicular to said single layer which provides said one of (a) and (b).

6. A device according to claim 1, wherein said single layer provides the shield layers of the two concentration cells, the first and second concentration cells being arranged generally symmetrically with respect to a plane parallel to said single layer.

7. A device to detect an actual air/fuel ratio of an air-fuel mixture subjected to combustion in a combustor based on the magnitude of an oxygen partial pressure in a combustion gas exhausted from the combustor, the device comprising:

(i) an oxygen sensing element which comprises;
 (a) a microscopically porous and gas permeable solid electrolyte layer of an oxygen ion conductive solid electrolyte, which is so shaped and sized as to serve as a structurally basic member of said element;
 (b) a gas permeable porous first measurement electrode layer formed on one side of said solid electrolyte layer;
 (c) a first reference electrode layer formed on the other side of said solid electrolyte layer so as to lie in a region generally opposite to said first measurement electrode layer;
 (d) a first shield layer of an electrochemically inactive material formed on said other side of said solid electrolyte layer such that microscopically said first reference electrode layer is entirely shielded from an environmental atmosphere by said solid electrolyte layer and said first shield layer;
 (e) a gas permeable porous second measurement electrode layer formed on said one side of said solid electrolyte layer;
 (f) a second reference electrode layer formed on said other side of said solid electrolyte layer so as to lie in a region generally opposite to said second measurement electrode layer; and
 (g) a second shield layer of an electrochemically inactive material formed on said other side of said solid electrolyte layer such that macroscopically said second reference electrode layer is entirely shielded from an environmental atmosphere by said solid electrolyte layer and said second shield layer;

(ii) first potentiometer means for measuring a first electromotive force generated across said first reference electrode layer and said first measurement electrode layer;

(iii) second potentiometer means for measuring a second electromotive force generated across said second reference electrode layer and said second measurement electrode layer; and (iv) DC power supply means for forcing a DC current of a first predetermined intensity to flow through said solid electrolyte layer from said first measurement electrode layer to said first reference electrode layer and a DC current of a second predetermind intensity through said solid electrolyte layer from said second reference electrode layer to said second measurement electrode layer.

8. A device according to claim 7, wherein said first predetermined intensity of the current is smaller than a first critical current intensity above which the magnitude of said first electromotive force becomes substantially constant so long as said air/fuel ratio remains above the stoichiometric air/fuel ratio of said air/fuel mixture, said second predetermined intensity of the current being smaller than a second critical value above which the magnitude of said second electromotive force becomes substantially constant so long as said air/fuel ratio remains below said stoichiometric air/fuel ratio.

9. A device according to claim 8, wherein said first and second reference electrode layers are united into a single electrode layer.

10. A device according to claim 8, wherein said first and second measurement electrode layers are united into a single electrode layer.

11. A device to detect an actual air/fuel ratio of an air-fuel mixture subjected to combustion in a combustor based on the magnitude of an oxygen partial pressure in a combustion gas exhausted from the combustor, the device comprising:
   (i) an oxygen sensing element which comprises;
      (a) a shield layer of an electrochemically inactive material, which is so shaped and sized as to serve as a structurally basic member of said element of said element;
      (b) a first reference electrode layer formed on said shield layer;
      (c) a microscopically porous and gas permeable first solid electrolyte layer formed on said shield layer such that macroscopically said first reference electrode layer is entirely shielded from an environmental atmosphere by said shield layer and said first solid electrolyte layer;
      (d) a gas permeable porous first measurement electrode layer formed on the outer side of said first solid electrolyte layer so as to lie in a region generally opposite to said first reference electrode layer;
      (e) a second reference electrode layer formed on said shield layer;
      (f) a microscopically porous and gas permeable second solid electrolyte layer formed on said shield layer such that macroscopically said reference electrode layer is entirely shielded from an environmental atmosphere by said shield layer and said second solid electrolyte layer; and
      (g) a gas permeable porous second measurement electrode layer formed on the outer side of said second solid electrolyte layer so as to lie in a region generally opposite to said second reference electrode layer;
   (ii) first potentiometer means for measuring a first electromotive force generated across said first reference electrode layer and said first measurement electrode layer;
   (iii) second potentiometer means for measuring a second electromotive force generated across said second reference electrode layer and said second measurement electrode layer; and
   (iv) DC power supply means for forcing a DC current of a first predetermined intensity to flow through said first solid electrolyte layer from said first measurement electrode layer to said first reference electrode layer and a DC current of a second predetermined intensity to flow through said second solid electrolyte layer from said second reference electrode layer to said second measurement electrode layer.

12. A device according to claim 11, wherein said first predetermined intensity of the current is smaller than a first critical value above which the magnitude of said first electromotive force becomes substantially constant so long as said air/fuel ratio remains above the stoichiometric air/fuel ratio of said air-fuel mixture, said second predetermined intensity being smaller than a second critical current intensity above which the magnitude of said second electromotive force becomes substantially constant so long as said air/fuel ratio remains below said stoichiometric air/fuel ratio.

13. A device according to claim 12, wherein said first and second reference electrode layers are formed respectively on the two opposite sides of said shield layer.

14. A device according to claim 12, wherein said first and second reference electrode layers are formed on the same side of said shield layer.

15. A device according to claim 14, wherein said first and second solid electrolyte layers are united into a single solid electrolyte layer.

16. A device according to claims 14 or 15, wherein said first and second reference electrode layers are united into a single electrode layer.

17. A device according to claims 14 or 15, wherein said first and second measurement electrode layers are united into a single electrode layer.

* * * * *